(12) United States Patent
Jevons

(10) Patent No.: US 8,281,666 B2
(45) Date of Patent: Oct. 9, 2012

(54) TEST APPARATUS AND METHOD

(75) Inventor: Matthew P. Jevons, Derby (GB)

(73) Assignee: Rolls-Royce PLC, London (GB)

( * ) Notice: Subject to any disclaimer, the term of this patent is extended or adjusted under 35 U.S.C. 154(b) by 215 days.

(21) Appl. No.: 12/822,316

(22) Filed: Jun. 24, 2010

(65) Prior Publication Data

US 2011/0000307 A1    Jan. 6, 2011

(30) Foreign Application Priority Data

Jul. 3, 2009 (GB) .................................. 0911504.9

(51) Int. Cl.
*G01N 3/08* (2006.01)

(52) U.S. Cl. ............................................. 73/818; 73/856

(58) Field of Classification Search .................... 73/818, 73/856–860
See application file for complete search history.

(56) References Cited

U.S. PATENT DOCUMENTS

| | | | | |
|---|---|---|---|---|
| 5,528,942 A | * | 6/1996 | Baratta | 73/856 |
| 5,546,817 A | * | 8/1996 | Heiman | 73/862.333 |
| 6,601,456 B1 | * | 8/2003 | Davidson et al. | 73/808 |
| 7,500,401 B2 | * | 3/2009 | Tsai | 73/859 |

FOREIGN PATENT DOCUMENTS

| | | |
|---|---|---|
| JP | A-2002-131203 | 5/2002 |
| RU | 2 020 453 C1 | 9/1994 |
| SU | 1037136 A | 8/1983 |
| WO | WO 98/21558 | 5/1998 |

OTHER PUBLICATIONS

British Search Report dated Sep. 10, 2009 in British Patent Application No. GB0911504.9.

* cited by examiner

*Primary Examiner* — Max Noori

(74) *Attorney, Agent, or Firm* — Oliff & Berridge, PLC

(57) ABSTRACT

The present invention relates to a Test apparatus (10) for testing the interaction between through-thickness compression and shear in a test piece (16). The apparatus comprises first and second chocks (12, 14) arranged in use to securely retain a test piece, and first and second races (18, 20) which can be controllably urged towards each other to transmit a known force to the first and second chocks. The first and second chocks and the test piece together form a substantially cylindrical body of a first diameter and. The first and second races define therebetween a substantially cylindrical space of a second diameter for accommodating the chocks, and wherein the second diameter is greater than the first diameter.

6 Claims, 3 Drawing Sheets

TEST APPARATUS AND METHOD

The present invention relates to apparatus and a method for testing the strength of a test piece, and is concerned particularly, although not exclusively, with apparatus and a method for testing the effect of through-thickness compression and shear in a composite test piece.

Previously, composite materials have been used in the aerospace industry mainly in secondary structural applications such as cowlings, panels and nose cones in order to provide a weight saving. However, composite materials are now being considered for primary components such as fan blades, guide vanes and casings.

As a result of these considerations it is becoming increasingly necessary to understand the behaviour of fibre reinforced composite materials in order to design components efficiently. Much is already well understood, and international testing standards already exist. However, through-thickness properties in particular still require more investigation.

One particular area about which more understanding is needed is how through-thickness compression and shear can interact in order to affect laminate failure. A shear failure is amongst the most critical failure modes in composites as shear can lead to de-lamination of the composite material, and possibly destruction of the component.

However, testing composite materials in their through-thickness direction has previously been difficult. By their nature, layered long-fibre-reinforced composites exhibit high performance in the plane in which they are laid up since it is this plane in which the long fibres run from which the composite material takes its strength. Out of this plane, or in the through-thickness direction, there are generally few or no fibres and therefore the composite relies upon the properties of the matrix material that joins and bonds the fibres together. Defining tests in the through-thickness direction requires specimens to be cut from panels which are normally relatively thin compared to their in-plane dimension. This in turn limits the potential size of the test pieces. Whilst thicker panels can be made, this has significant cost and time implications. For example, even a 30 mm thick sample of composite panel may require the laying down of up to 120 layers which might only be laid four at a time before placing them in a vacuum container for a period of up to half an hour. Moreover the earlier layers may begin to cure before the upper layers are laid, which can affect the characteristics of the composite sample. Unfortunately, a relatively thick sample of composite material is required in order to make a coupon or test piece since the test results will vary in dependence upon the thickness of the coupon.

Previous attempts have been made to test composites in their through-thickness direction under direct tension, compression or shear. Through-thickness tension can be measured using a simple method in which a thick-waisted specimen of approximately 25 mm thickness is loaded into grips and pulled apart. An alternative method uses an L-shaped sample which is loaded under four point bending and pushed downwards to failure at the "heel" section. Through-thickness compression can also be measured using a waisted specimen but loaded under compression. Careful attention has to be given to ensure when compressive loading is placed upon the sample that there is sufficient height to allow appropriate compression shear planes to develop, yet not so much thickness that the specimen begins to buckle.

Through-thickness shear can be measured using for example the "Iosipescu" test in which a V-notched coupon, or sample has a load applied to it through a pair of grips. In addition, the so-called "Arcan" method was developed to quantify the interaction between tension and shear in the through-thickness direction. The coupon or test piece is cut from a thick panel and is waisted on two opposing sides. The coupon is then loaded into a rig assembly that allows different ratios of tension and shear to be applied. The Arcan test is able to address the interaction between tension and shear and has on occasion been used to test for the interaction between compression and shear. However, it requires a thick composite panel as the parent material for the coupons. As previously explained thick panels are expensive and difficult to manufacture reliably. Furthermore, machining the specific shape of the coupon is also difficult as a large amount of machining is done in the weakest direction of the composite and therefore there is a high chance that damage might occur in the specimen during machining and lead to unreliable test results.

Composites also need to be evaluated at elevated temperature and moisture conditions as their properties are often compromised by either of these parameters. Thick specimens, which are required in the previously considered test methods described above, can take a long time to condition to the desired level of moisture. For example, preparing a specimen to the required moisture condition can involve placing the coupon in a conditioning chamber for several months.

Accordingly, embodiments of the present invention aim to provide a test apparatus and method in which the above-mentioned drawbacks are at least partly overcome.

The present invention is defined in the attached independent claims to which reference should now be made. Further preferred features may be found in the sub-claims appended thereto.

According to the invention there is provided test apparatus for testing the interaction between through-thickness compression and shear in a test piece, the apparatus comprising first and second chocks arranged in use to securely retain a test piece, and first and second races which can be controllably urged towards each other to transmit a known force to the first and second chocks, wherein the first and second chocks and the test piece together form a substantially cylindrical body of a first diameter and wherein the first and second races define therebetween a substantially cylindrical space of a second diameter for accommodating the chocks, and wherein the second diameter is greater than the first diameter.

Preferably the substantially cylindrical body formed by the chocks and test piece is rotatable within the substantially cylindrical space defined by the first and second races so as to allow a test piece to experience different combinations of compression and shear according to the orientation of the chocks in the races.

The invention also includes a method of testing the interaction between through-thickness compression and shear in a test piece, the method comprising mounting the test piece between first and second chocks shaped such that the chocks and test piece together form a substantially cylindrical body having a first diameter, mounting the chocks and test piece between first and second races which define a substantially cylindrical space therebetween of a second diameter, greater than the first diameter, and urging the races towards each other so as to apply a known force to the chocks.

The method preferably further comprises rotating the chocks and the test piece within the substantially cylindrical space defined by the races so as to vary the combination of compression and shear which acts upon the test piece.

A preferred embodiment of the present invention will now be described by way of example only with reference to the accompanying drawings, in which.

Figures 1A, 1B:
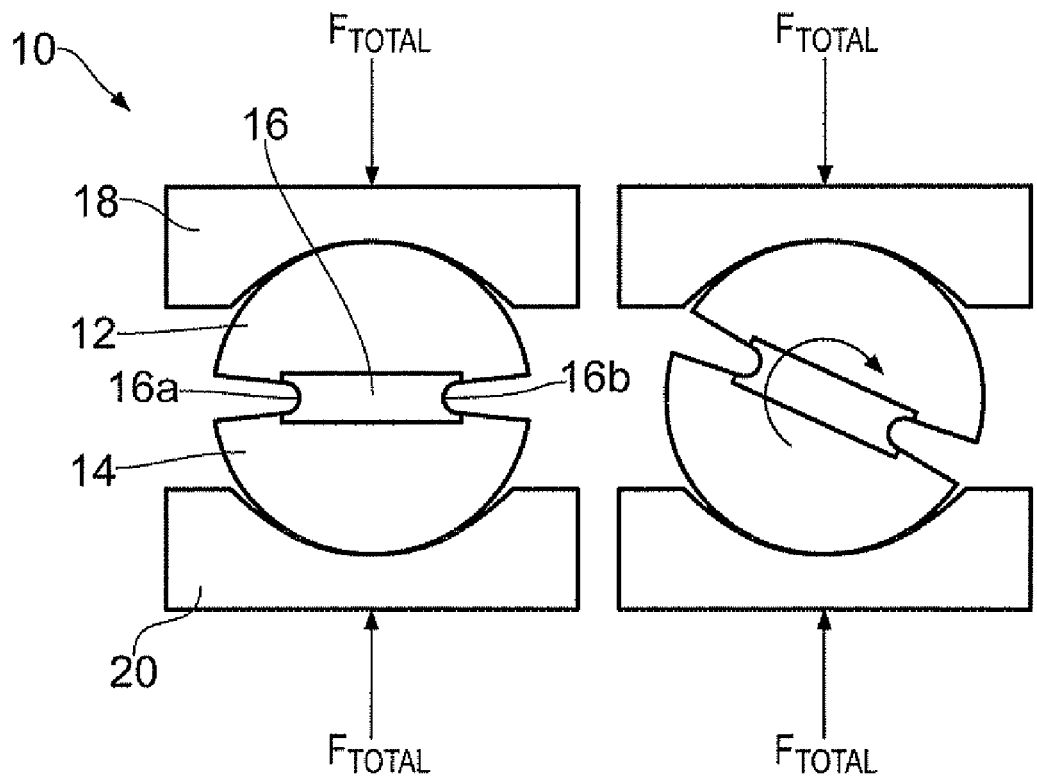
FIG. 1a shows schematically a test apparatus according to an embodiment of the present invention.
FIG. 1b shows schematically the test apparatus of FIG. 1a in an alternative configuration.

Turning to FIGS. 1a and 1b, test apparatus, for testing the interaction between compression and shear forces in through-thickness loading of composite laminates is shown generally at 10. The apparatus comprises a pair of chocks 12, 14 which retain between them a coupon, or test specimen, 16 of carbon-fibre laminate. Though not shown in the drawings the orientation of the layers of laminate is such that they are horizontal in FIG. 1a. The coupon 16 in this example is formed of 5 mm laminate but it could be made from other thicknesses of laminate, such as from 4 mm to 25 mm. Its in-plane dimensions are 20 mm long and 10 mm wide, though these dimensions could be greater or less. The coupon 16 is notched at opposed ends 16a and 16b. In this embodiment a constant 1.5 mm radius is used, although a V-notch or saw cut could be used. The coupon is loaded into the opposed chocks 12, 14 and assembled together with the coupon they form a generally cylindrical body.

The coupon and chock assembly fits between two opposing races 18, 20 wherein the radius of the races is greater than the radius of the cylindrical body formed by the coupon and the chocks.

Having a cylindrical assembly of coupon and chocks allows the entire assembly to be rotated within the races as is shown in FIG. 1b. This in turn makes it possible to combine compression and shear in varying amounts. The preferred solution in this embodiment is to allow the cylinder formed by the coupon and the chocks to rotate in 5 degree increments. Having the radius of the races greater than that of the cylinder ensures that there is a single, controllable contact point during the test. The single contact point avoids translation of any misalignment of the races into the coupon which can give rise to erroneous readings. Force is applied to the cylinder from the races and is transmitted to the coupon.

Figure 2:
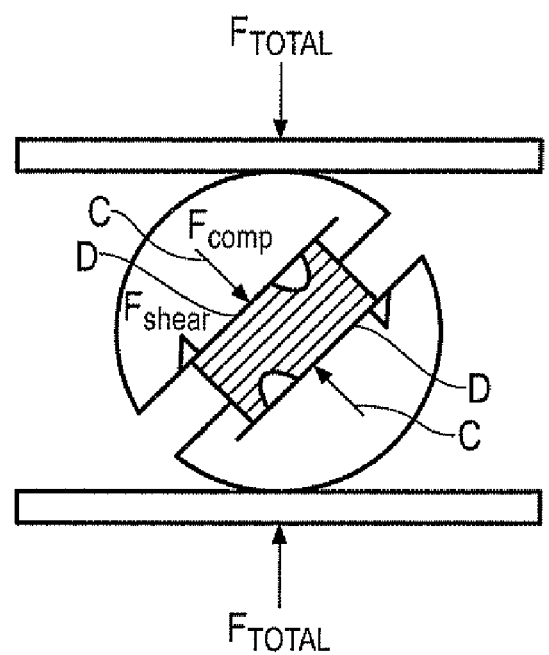
FIG. 2 shows the test apparatus of FIGS. 1a and 1b with annotations to show how forces are applied.

FIG. 2 illustrates a different embodiment and the different forces acting upon the coupon 16 of FIGS. 1a and 1b. Arrows C illustrate the direction of the compressive force component $F_{COMP}$ and arrows D illustrate the direction of the shear force component $F_{SHEAR}$. The races in this embodiment are plates with flat surfaces facing and contacting the chocks at the single contact point.

Figure 3:
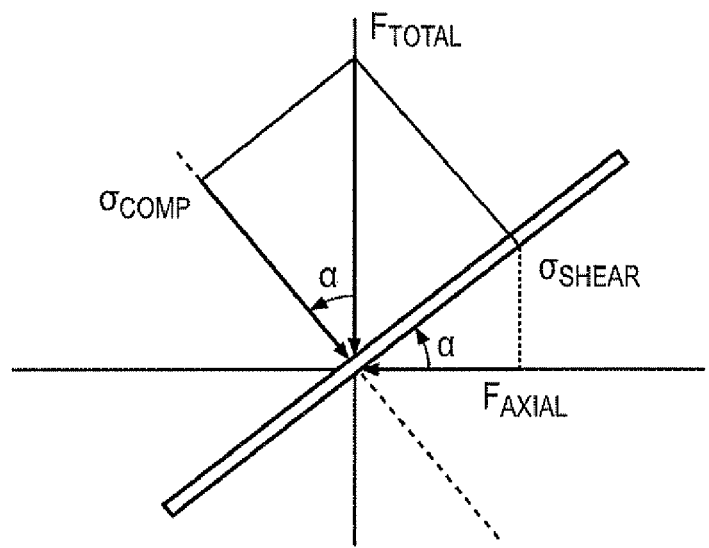
FIG. 3 is a diagram which further illustrates the forces shown in FIG. 2.

FIG. 3 illustrates the compressive stress $\sigma_{COMP}$ and shear stress $\sigma_{SHEAR}$ acting upon the coupon of FIG. 2. As is shown in FIG. 3, rotating the chocks resolves the total compressive force $F_{TOTAL}$ exerted by the test apparatus into compressive and shear force components $F_{COMP}$ and $F_{SHEAR}$. The angle of rotation of the cylindrical body formed by the chocks and the coupon with respect to the races, controls the ratio of compressive and shear forces acting upon the coupon.

With reference again to FIG. 3 simple trigonometry shows that:

$$F_{SHEAR} = F_{TOTAL} \cdot \sin(\alpha)$$

and $$F_{COMP} = F_{TOTAL} \cdot \cos(\alpha)$$

Given the area of the specimen (l) multiplied by the thickness (t) the shear and compressive stresses can be determined as follows:

$$\sigma_{SHEAR} = \frac{F_{SHEAR}}{l \cdot t} \text{ and } \sigma_{COMP} = \frac{F_{COMP}}{l \cdot t}$$

To test the specimen the total load at failure ($F_{FAIL}$) can be determined for every angle between 0° and 90°.

Figure 4:
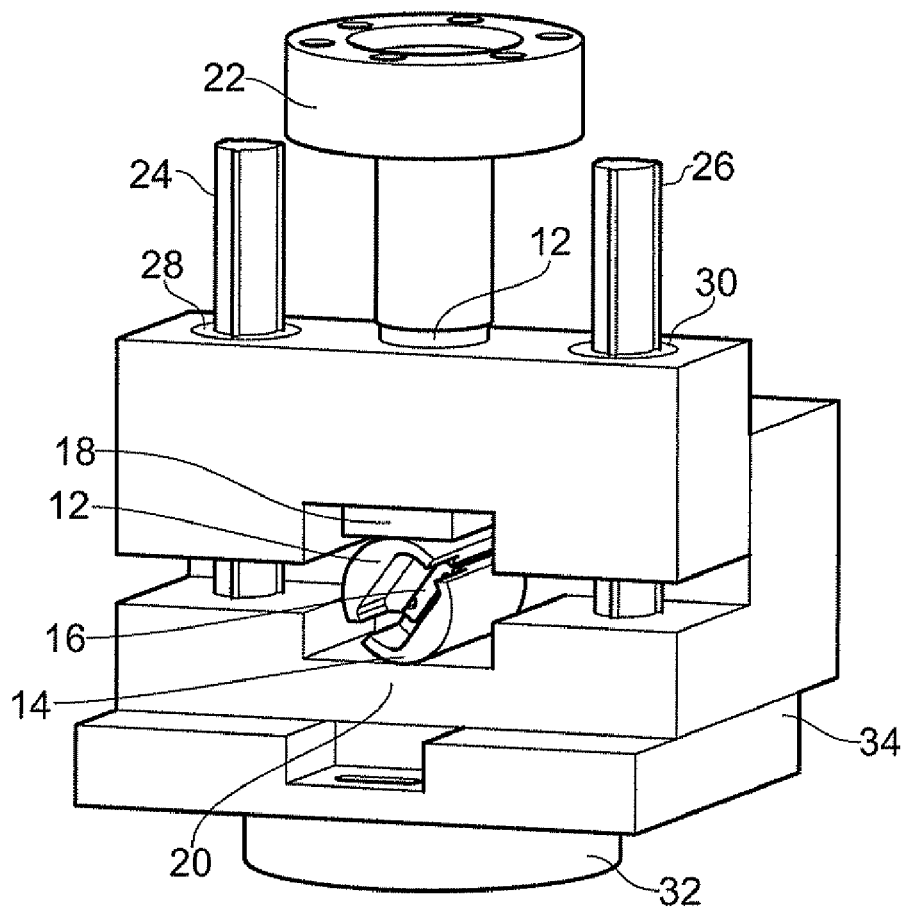
FIG. 4 shows the test apparatus of FIGS. 1-3 in perspective view.

FIG. 4 shows in perspective view an example of apparatus for testing shear and composite stress in accordance with the embodiment described in relation to FIGS. 1-3. The apparatus shown in FIG. 4 comprises a top fixture 22 first and second spline shafts 24, 26 and respective spline ball bearings 28, 30, a bottom fixture 32 and base plate 34, upper and lower races 18, 20, upper and lower chocks 12, 14 and coupon 16.

Figure 5:
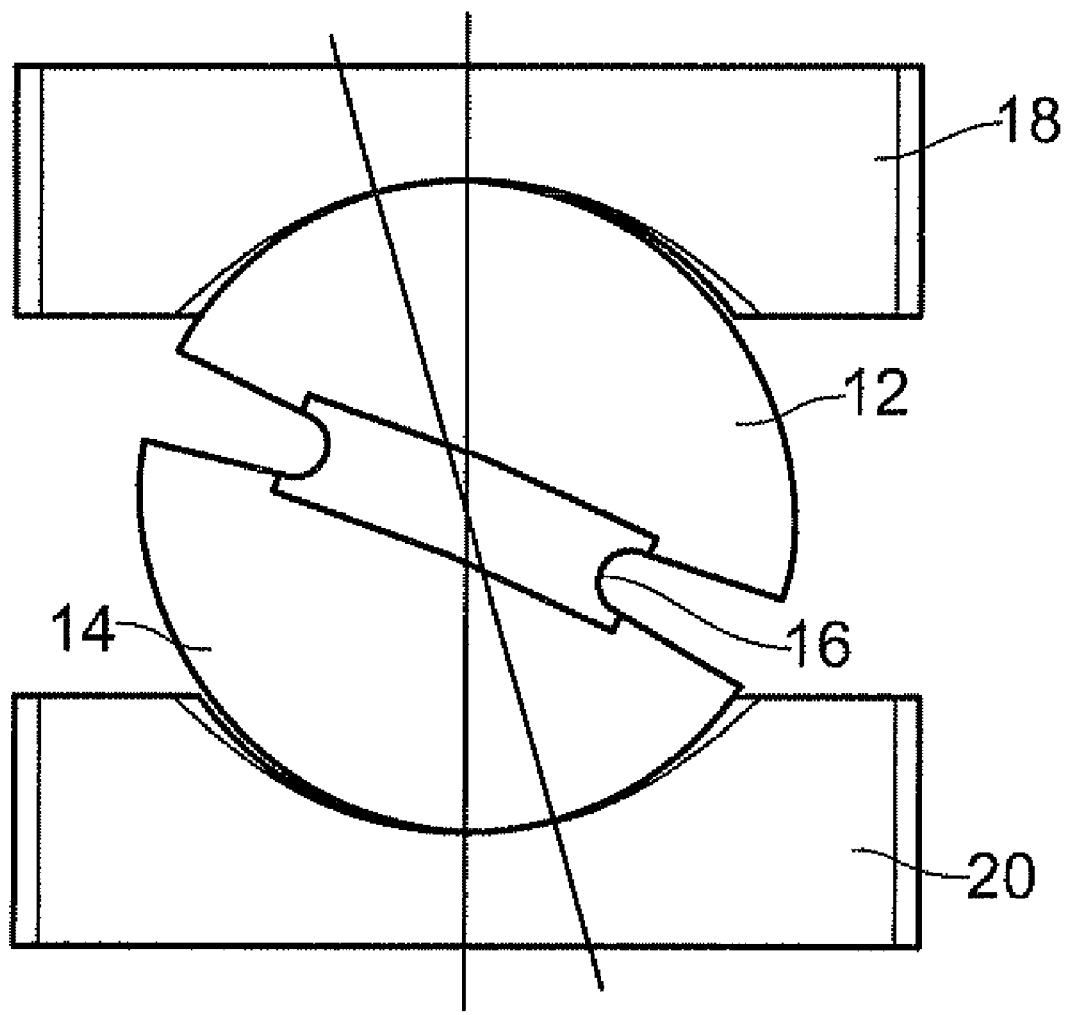
FIG. 5 shows schematically the test apparatus of FIGS. 1-3 in a further, alternative configuration.

Giving lateral control to the races gives access to further loading angles outside the 5 degree increments and allows the fine tuning of the alignment of the loading points. The provision of a single respective contact point between the chocks and the races ensures that the load path passes through the center of the coupon, as is illustrated in FIG. 5 in which the races are laterally shifted either intentionally or through misalignment.

In the embodiment described above the chocks and races are made from steel, but another material could be used which is capable of sustaining the applied load without failure.

A significant advantage of the present invention, when compared with previous apparatus types, is that it allows evaluation of how failure changes when compression and shear loading are combined into a composite. The use of a 5 mm coupon size makes it possible to easily condition the coupons to the desired moisture and temperature levels, a length-to-thickness aspect ratio in the coupon of 4:1 makes for a more robust coupon in machining (i.e. one which is less susceptible to deviations in the machined notches and where there is less risk of imparting damage whilst machining). The test apparatus described herein is suitable for the testing of both unidirectional ply level coupons and also multi-angular laminates.

The sides of the coupon can be strain-gauged to allow strain measurements, or else can be visually accessed to use other strain measurement techniques. Furthermore the apparatus can readily fit into a standard compression testing machine.

The method in accordance with the invention can be further extended to a three-dimensional interaction in which compression interacts with both through-thickness shear planes (1-3 and 2-3) by using a spherical chock configuration as opposed to a cylindrical chock configuration as shown in the Figures. Fine alignment of the races can then be achieved for orthogonal adjusters. In this case the coupon needs to be either rectangular with all of its sides notched or else circular with a notch going all the way around the circumference.

The test can also be adapted to test sandwich structures and bonded joints as well as other composites, not just carbon-fibre composites which are described herein.

The invention claimed is:

1. Test apparatus for testing the interaction between through-thickness compression and shear in a test piece, the apparatus comprising first and second chocks arranged in use to securely retain a test piece, and first and second races which can be controllably urged towards each other to transmit a known force to the first and second chocks, wherein the first and second chocks and the test piece together form a substantially cylindrical body of a first diameter and wherein the first and second races define therebetween a space for accommodating the chocks, and are arranged to provide a single, controllable contact point between the first chock and the first race and a single controllable contact point between the second chock and the second race.

2. Test apparatus according to claim 1 wherein the substantially cylindrical body formed by the chocks and test piece is rotatable within the space defined by the first and second races so as to allow a test piece to experience different combinations of compression and shear according to the orientation of the chocks in the races.

3. Test apparatus according to claim 1, wherein the races have respective surfaces adapted to face the chocks wherein each surface comprises a depression arranged such that the single controllable contact point between the race and the chock is sited within the depression.

4. Test apparatus according to claim 3 wherein the depression has a radius, the radius of the depression being greater than the radius of the chocks.

5. A method of testing the interaction between through-thickness compression and shear in a test piece, the method comprising mounting the test piece between first and second chocks shaped such that the chocks and test piece together form a substantially cylindrical body having a first diameter, mounting the chocks and test piece between first and second races which define a space therebetween and arranged to provide a single, controllable contact point between the first chock and the first race and a single controllable contact point between the second chock and the second race, and urging the races towards each other so as to apply a known force to the chocks.

6. A method according to claim 5 further comprising rotating the chocks and the test piece within the space defined by the races so as to vary the combination of compression and shear which acts upon the test piece.

\* \* \* \* \*